(12) United States Patent
Pavlovsky

(10) Patent No.: US 11,112,384 B2
(45) Date of Patent: *Sep. 7, 2021

(54) METHANE GAS SENSOR

(71) Applicant: Applied Nanotech, Inc., Austin, TX (US)

(72) Inventor: Igor Pavlovsky, Cedar Park, TX (US)

(73) Assignee: Applied Nanotech, Inc., Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/810,325

(22) Filed: Mar. 5, 2020

(65) Prior Publication Data
US 2020/0249202 A1 Aug. 6, 2020

Related U.S. Application Data

(63) Continuation of application No. 16/277,820, filed on Feb. 15, 2019, now Pat. No. 10,627,368.
(Continued)

(51) Int. Cl.
G01N 29/02 (2006.01)
H05K 1/18 (2006.01)
H05K 5/06 (2006.01)
H05K 7/20 (2006.01)
H05K 5/00 (2006.01)
(Continued)

(52) U.S. Cl.
CPC ......... *G01N 29/022* (2013.01); *G01N 29/036* (2013.01); *G01N 29/326* (2013.01); *G01N 33/0047* (2013.01); *G01N 33/0063* (2013.01); *G08B 21/16* (2013.01); *H05K 1/18* (2013.01); *H05K 5/0008* (2013.01); *H05K 5/069* (2013.01); *H05K 7/20* (2013.01);
(Continued)

(58) Field of Classification Search
CPC .. G01N 29/022; G01N 29/036; G01N 29/326; G01N 33/0047; G01N 33/0063; G08B 21/16; H05K 1/18; H05K 5/0008; H05K 5/069; H05K 7/20
USPC ....................................................... 340/632
See application file for complete search history.

(56) References Cited

U.S. PATENT DOCUMENTS

| 10,627,368 B2 * | 4/2020 | Pavlovsky | ............. | G08B 21/16 |
| 2005/0145019 A1 * | 7/2005 | Matsiev | ................. | G01N 11/16 73/53.01 |

(Continued)

Primary Examiner — Kerri L McNally
(74) Attorney, Agent, or Firm — Sutton Magidoff Barkume LLP

(57) ABSTRACT

An apparatus and method for detection of methane in an environment, including a housing with a sensor printed circuit board and a processor printed circuit board interconnected to and thermally insulated from the sensor printed circuit board. The sensor printed circuit board includes a first tuning fork isolated from the environment, and a second tuning fork exposed to the environment. The tuning forks are attached to opposite sides of the sensor printed circuit board. The processor printed circuit board includes processing circuitry interconnected to the first tuning fork and the second tuning fork, which receives vibration frequency signals therefrom, and is programmed to determine a frequency difference between the frequency of vibration of the first tuning fork and the frequency vibration of the second tuning fork, and if the frequency difference is greater than a predetermined threshold, then setting an alarm to indicate the presence of methane.

12 Claims, 12 Drawing Sheets

Related U.S. Application Data

(60) Provisional application No. 62/631,756, filed on Feb. 17, 2018.

(51) Int. Cl.
| | | |
|---|---|---|
| *G01N 33/00* | (2006.01) | |
| *G01N 29/036* | (2006.01) | |
| *G01N 29/32* | (2006.01) | |
| *G08B 21/16* | (2006.01) | |

(52) U.S. Cl.
CPC .............. *H05K 2201/10022* (2013.01); *H05K 2201/10083* (2013.01); *H05K 2201/10151* (2013.01)

(56) References Cited

U.S. PATENT DOCUMENTS

| | | | |
|---|---|---|---|
| 2014/0331766 A1* | 11/2014 | Kramer | G01N 11/16 73/32 A |
| 2016/0061784 A1* | 3/2016 | Madhav | G01N 21/1702 73/24.02 |
| 2017/0038343 A1* | 2/2017 | Kshirsagar | G01N 29/036 |

* cited by examiner

METHANE GAS SENSOR

TECHNICAL FIELD

This invention relates generally to the detection of methane gas, and in particular to a methane/natural gas sensor for residential applications.

BACKGROUND

Currently available methane detectors have a problem with false alarms, where the sensors are sensitive to not only methane but also to other materials in the air such as hairspray. As a result of such false detection, present day detectors are unreliable, and the present invention solves this problem as described herein.

SUMMARY

Provided herein is a methodology for using two tuning forks as part of a device, where one of the tuning forks is isolated from the environment that is being monitored. This control tuning fork will be within a vacuum and it will be heated so that temperature and pressure are controlled. The second (isolated) tuning fork is exposed to the ambient environment so that if methane is detected in the environment, a comparison is made of the frequency of vibration between the ambient-exposed tuning fork and the isolated tuning fork. By sensing the difference between the frequency of vibrations of the two tuning forks, the present invention determines if methane is present and causes an alarm to go off.

DETAILED DESCRIPTION OF THE PREFERRED EMBODIMENTS

Figure 1:
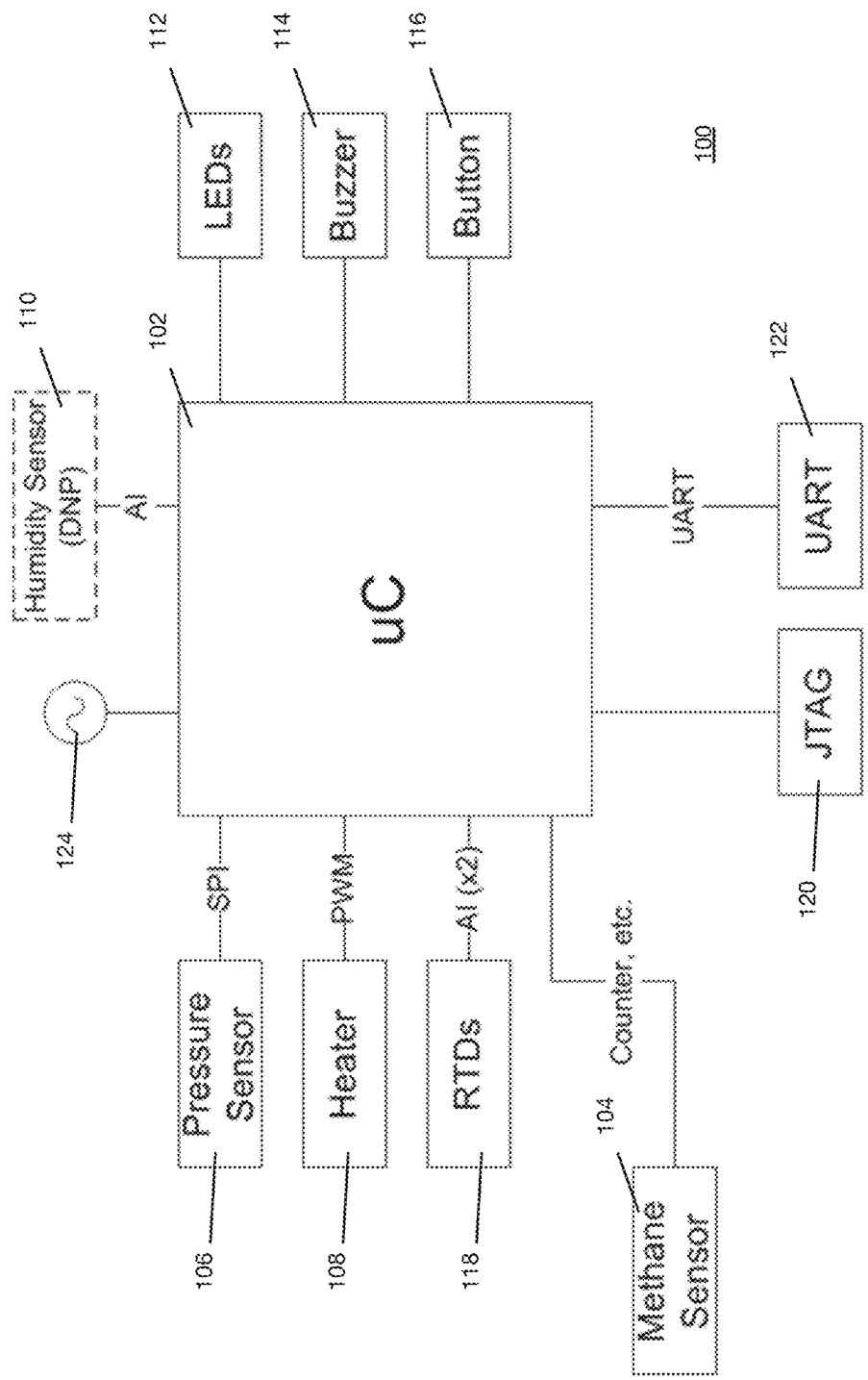
FIG. 1 is a block diagram of the circuitry of the methane detector of the preferred embodiment.

The operation of the sensor is based on the assessment of the molar mass of a gas mixture wherein the effective molar mass of the monitored gas decreases in the presence of low mass methane molecules. The lower molar mass of the monitored gas mixture results in higher frequency of oscillations of a quartz resonator open to the monitored environment, such as a quartz tuning fork.

A pressure sensor is used to compensate against atmospheric pressure variations and calculate the correct molar mass of the gas mixture. The oscillation frequency of the open resonator shifts with gas pressure changes as well as with the variations in the methane concentration in air within the methane concentration range from 0% to 100%.

A second quartz oscillator can be used as a reference element wherein this second oscillator can be open to an atmosphere which does not contain methane, or the said oscillator can be vacuum sealed by manufacturer. In this case, a differential frequency between the two oscillators is a function of the methane concentration in a gas mixture.

In a preferred embodiment, the differential frequency can be obtained using a D flip-flop trigger. Signals from the two oscillators are connected to the two inputs (D input and Clock input) of the trigger. The trigger output producing the differential frequency signal is a low frequency signal. This signal modulates an external continuous high frequency signal (carrier frequency), and the number of the pulses modulated by the sensor differential frequency is counted. The number of pulses can be counted every second. The number of pulses is a nearly linear function of the methane concentration.

To improve the sensor stability against temperature variations, the quartz tuning fork resonators are kept at a constant temperature using external heating elements. Temperature sensing elements such as thermistors can be used in the temperature control loop, while the heating elements can be resistors mounted next to the oscillators.

Since the oscillators and the thermistors have physically different locations, it is possible that the second order temperature deviations may occur in the oscillator if the ambient temperature changes. However, it is safe to assume that these small oscillator temperature variations are linear functions of the ambient temperature within a working temperature range of the methane sensor.

As the thermistors are used in the temperature control loop, their temperature (or control resistance) is always fixed. In order to assess the actual oscillator temperature deviations, a heating power or a sensor heater PWM duty factor can be used for the temperature compensation.

In order to further improve the sensor stability in different environments, an external humidity sensor can be used to compensate against variations in relative humidity. However, in normal operation conditions inside residential buildings the use of the humidity sensor may not be needed.

Thus, knowing that the sensor signal depends essentially linear on the ambient pressure, temperature, and the methane concentration, it is possible to use an easy for computation first order concentration calculation formula such as below:

$$C=[(dF-D)*(101325/p)+c1*PWM+c2*RH]/S, \quad [1]$$

where C is the methane concentration, dF is the number of pulses, p is atmospheric pressure in kPa, PWM is the heater duty factor, RH is the relative humidity, S is the sensor span, D is a parameter accounting for the sensor response to pressure and the sensor drift, and c1 and c2 are calibration coefficients.

The unknown coefficients as well as the sensor span are obtained thought the sensor calibration. The calibration procedure consists of at least two-point sensor tests such as at two different temperatures, two different pressures, and two different concentrations, wherein one of the set points can be a room temperature, an atmospheric pressure, and 0% methane concentration.

To further simplify the test procedure, it is possible to use the sensitivity of the methane sensor to pressure variations for determination of the sensor sensitivity to methane (sensor span). From the formula [1], we can see that $$S \sim k*dF/dp, \quad [2]$$

where k is a constant.

The sensor drift is due to slow oxidation of the quartz resonator electrodes and resonator surface coating with dust, tar, or chemicals. In order to compensate for the slow drift, an auto-zero function can be implemented in the sensor, such as a high pass filter. In a preferred embodiment, the high pass filter is implemented in the sensor firmware, it can transmit signals with the time constant on the order of hours and reject slow sensor drift with a time constant on the order of days.

In a preferred embodiment, the methane sensor comprises two oscillators each of which have a quartz tuning fork resonator. One of the two tuning forks is open to the environment, the other one is factory sealed. The two oscillators are located next to each other, preferably on the opposite sides of a sensor printed circuit board (PCB). The sensor printed circuit board having the oscillators is thermally insulated from the main processor circuit board by narrow contact bridges. The sensor printed circuit board has SMD heating elements that are powered via the temperature control loop to keep the temperature of the oscillators at around 55 C.

To further improve the thermal insulation and minimize convection losses, the sensor PCB is enclosed within a porous thermally insulating material. The porous material is gas permeable, and it inhibits air convection around the sensor PCB. The thermally insulating enclosure helps decrease thermal losses and power consumption by the methane sensor.

The sensor is based on an MSP430 microprocessor, has a push button, three status LEDs, sound alarm, wall plug power supply, back-up battery, and is designed to conform the UL 1484 standard.

Figure 2:
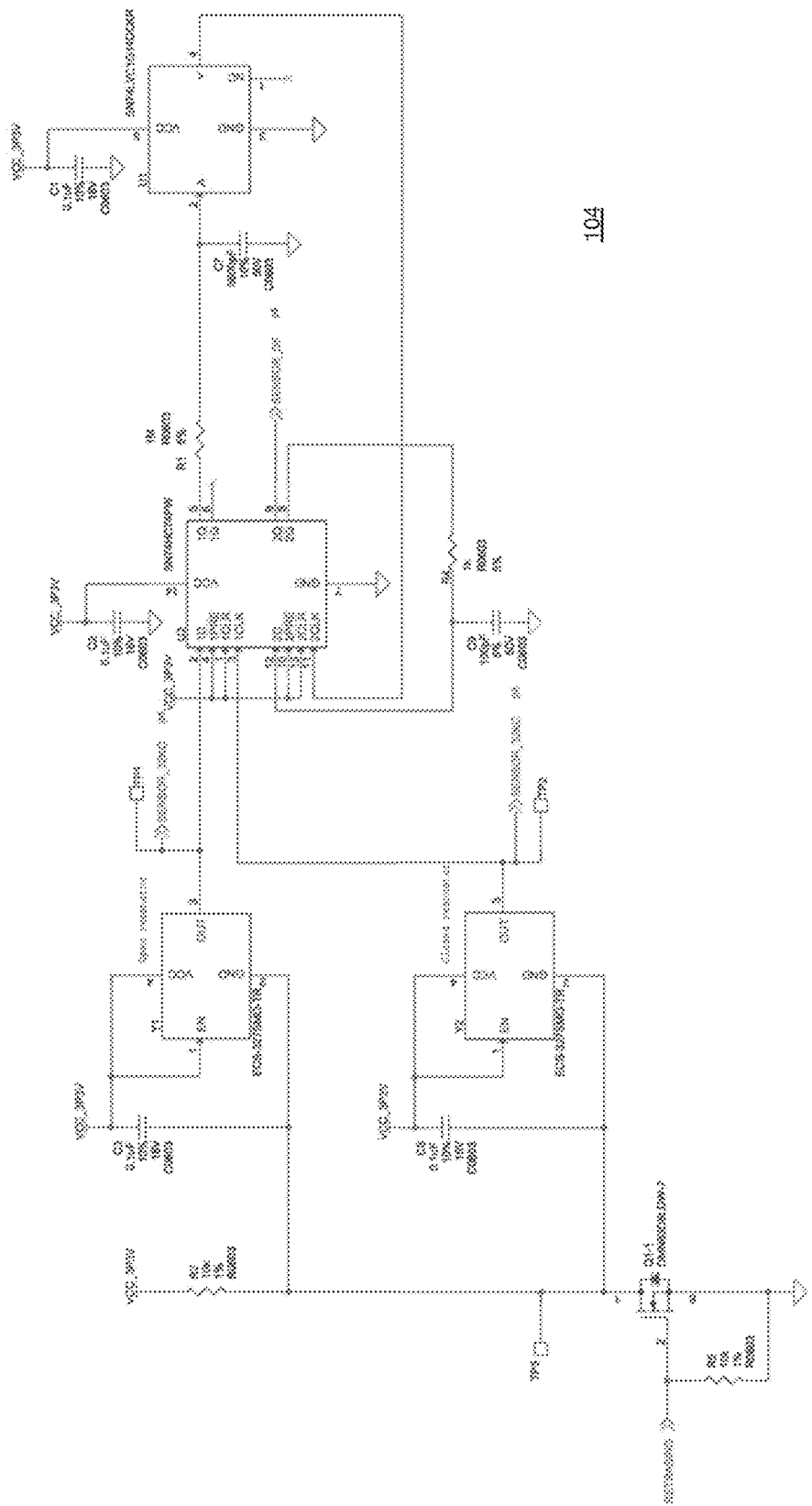
FIG. 2 is a detailed schematic of the methane sensor sub-circuit of the methane detector of FIG. 1.
Figure 3:
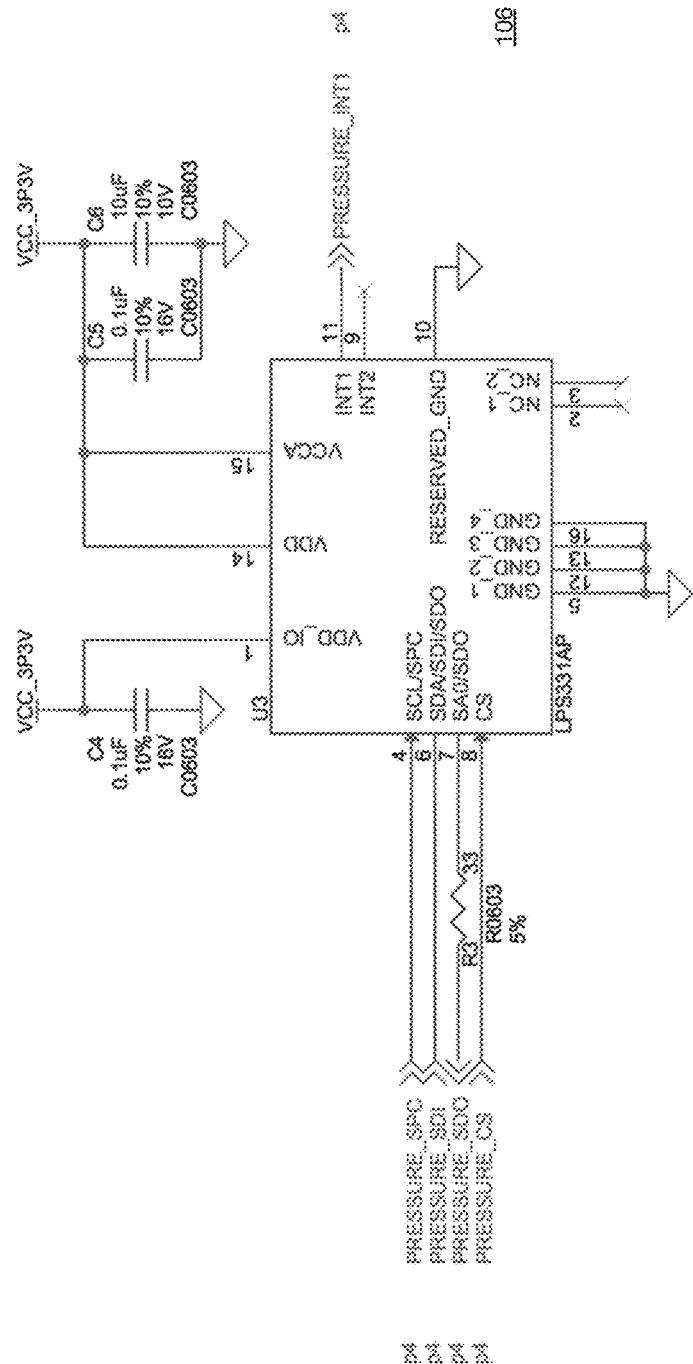
FIG. 3 is a detailed schematic of the pressure sensor sub-circuit of the methane detector of FIG. 1.
Figure 4:
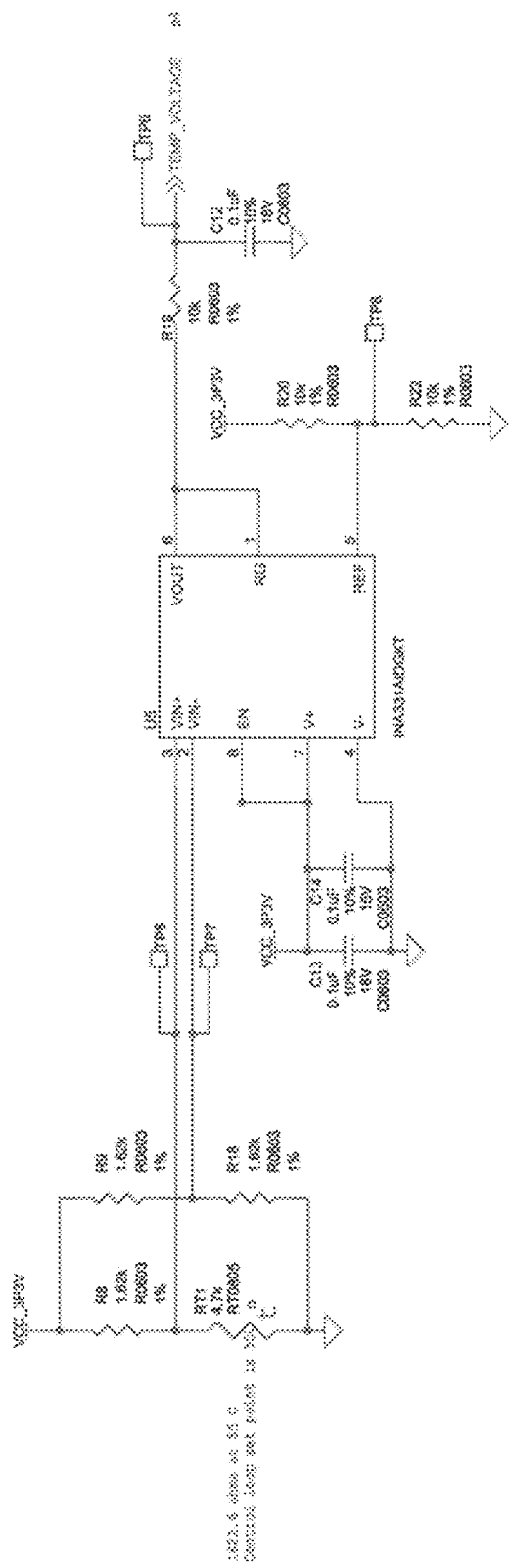
FIG. 4 is a detailed schematic of a temperature sensor sub-circuit of the methane detector of FIG. 1.
Figure 5:
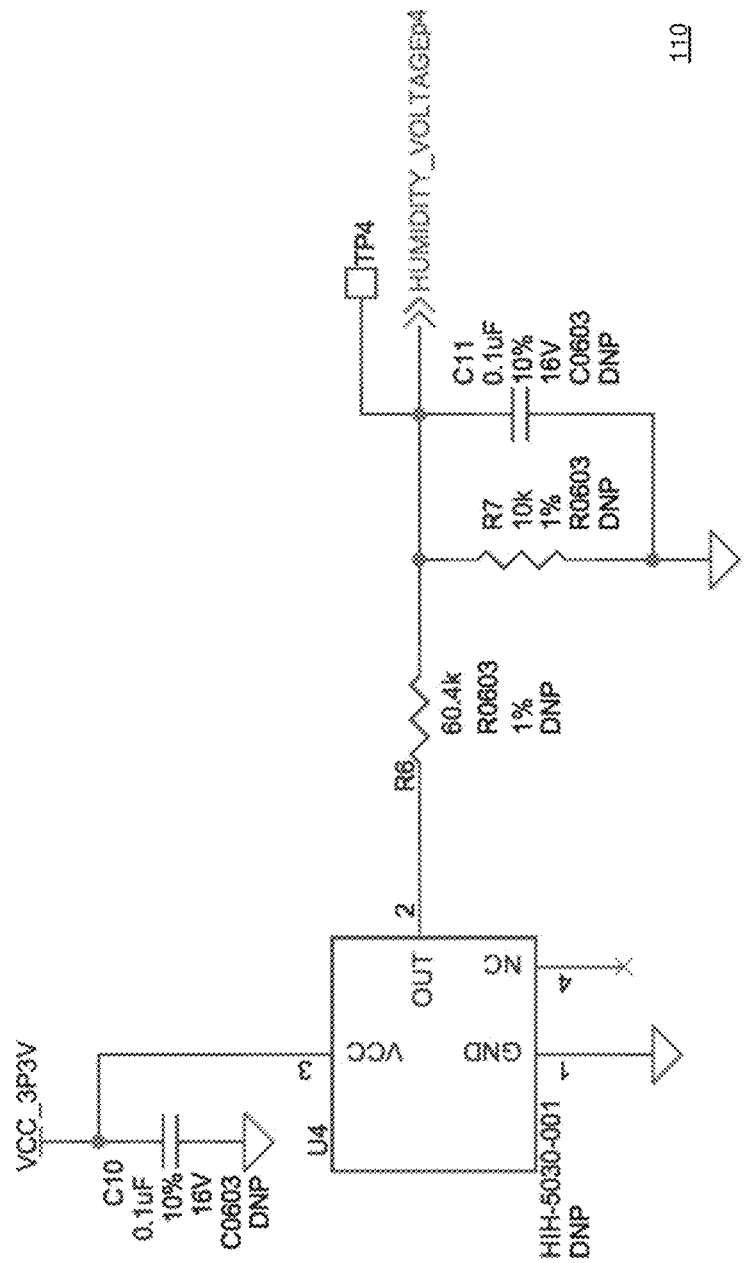
FIG. 5 is a detailed schematic of the humidity sensor sub-circuit of the methane detector of FIG. 1.
Figure 6:
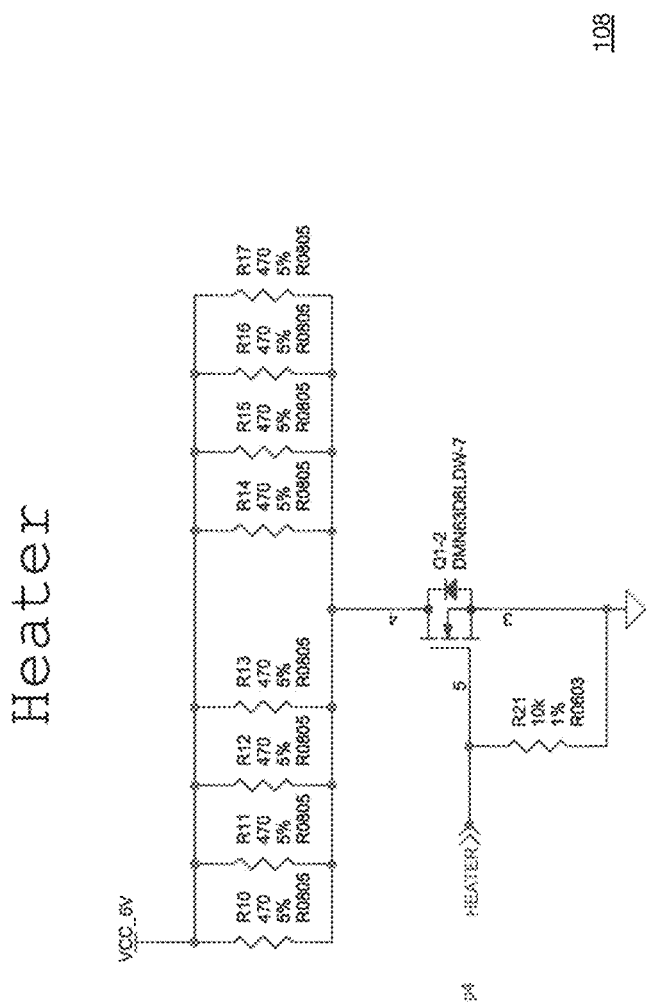
FIG. 6 is a detailed schematic of the heater sub-circuit of the methane detector of FIG. 1.

Reference is now made to FIG. 1, which is a block diagram of the circuitry 100 of the methane detector of the preferred embodiment. Shown in FIG. 1 is a microcontroller 102 that is connected to a methane sensor sub-circuit 104 (see FIG. 2), a pressure sensor sub-circuit 106 (see FIG. 3), a humidity sensor sub-circuit 110 (see FIG. 5), a heater sub-circuit 108 (see FIG. 6), LEDs 112, a buzzer 114, a button 116, RTDs 118, JTAG 120, UART (universal asynchronous receiver-transmitter) 122, and oscillator 124.

Figure 7:
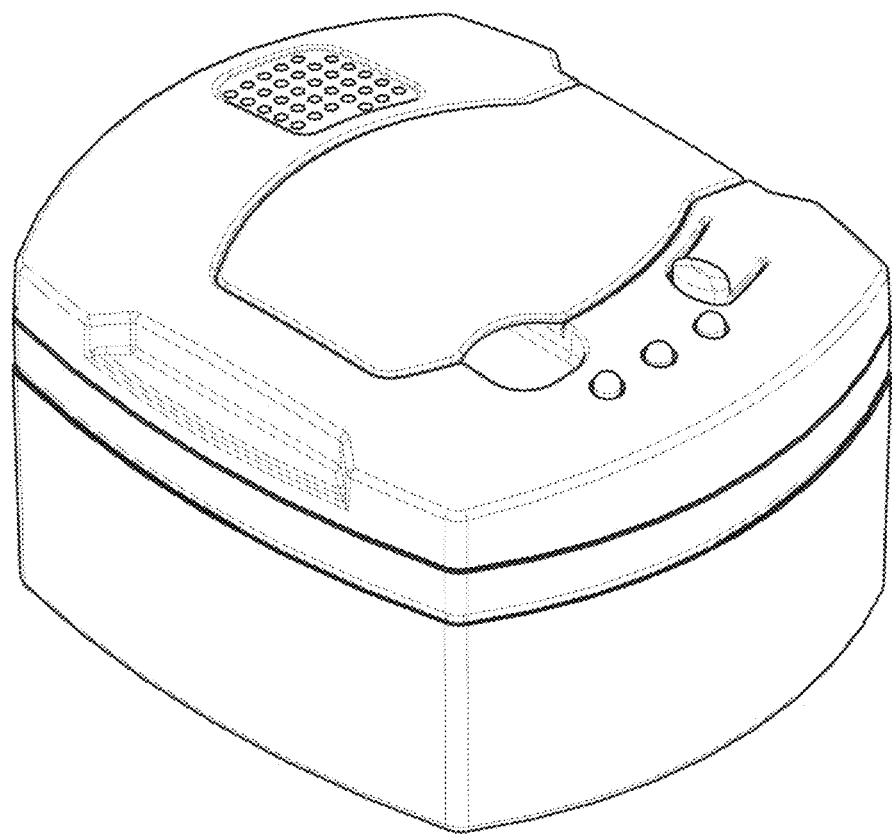
FIG. 7 is a perspective illustration of the methane sensor in a plastic housing (fully assembled).
Figure 8:
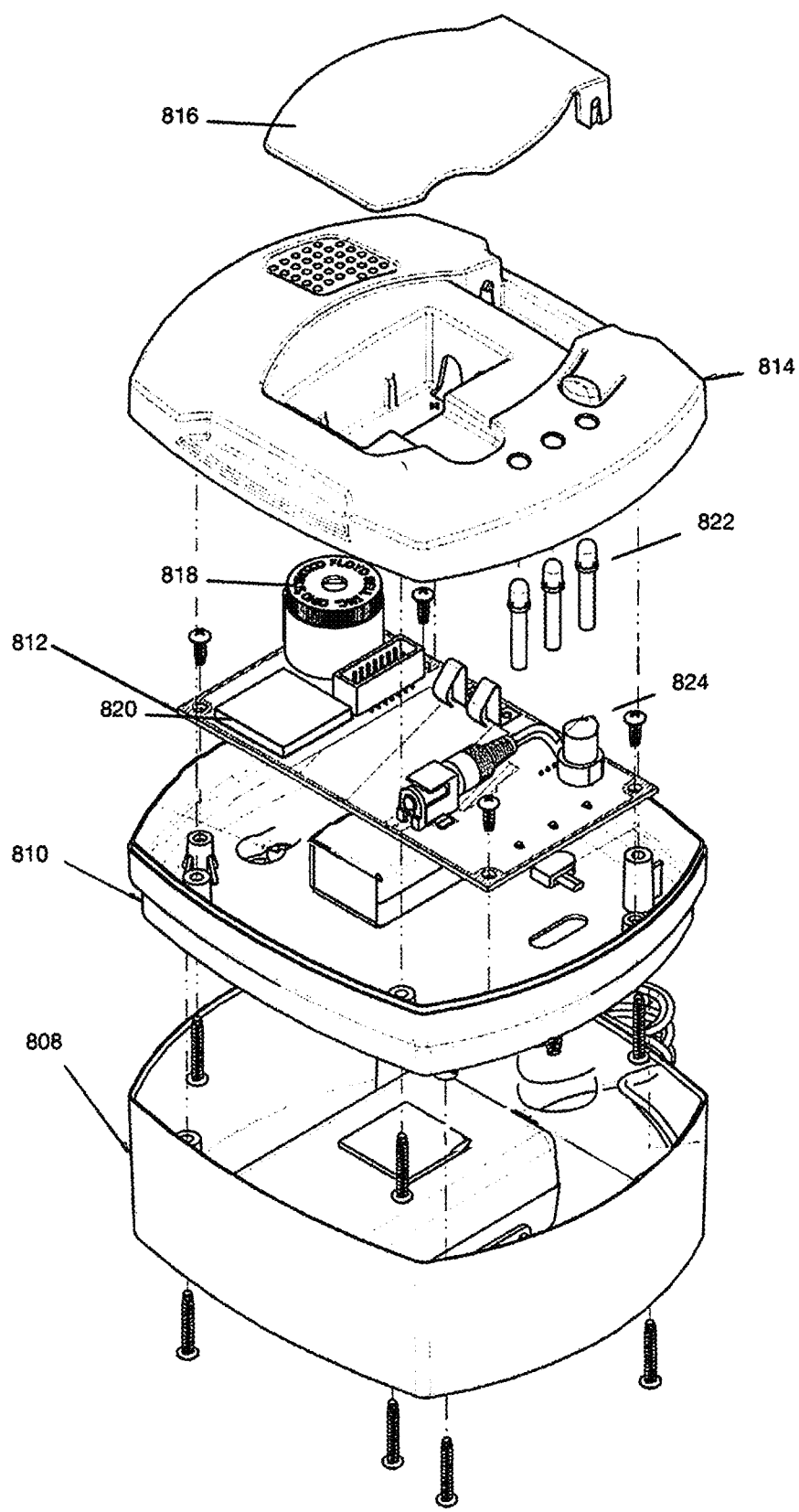
FIG. 8 is an exploded view of the methane sensor of FIG. 7.

FIG. 7 shows a perspective illustration of the methane sensor in a plastic housing, in fully assembled form, while FIG. 8 is an exploded view of the methane sensor of FIG. 7. Major components include a housing 808, a base 810 that is affixed to the housing 808, and a PC board 812 that is affixed to the base 810 as shown. The PC board 812 holds the electronic components including for example the resonator under thermal insulation 820, push-button 824, a buzzer 818 and several LEDs 822 (e.g. power and alarm indicators). This assembly is protected by the top cover 814 and a battery cover 816 as shown.

Figure 9:
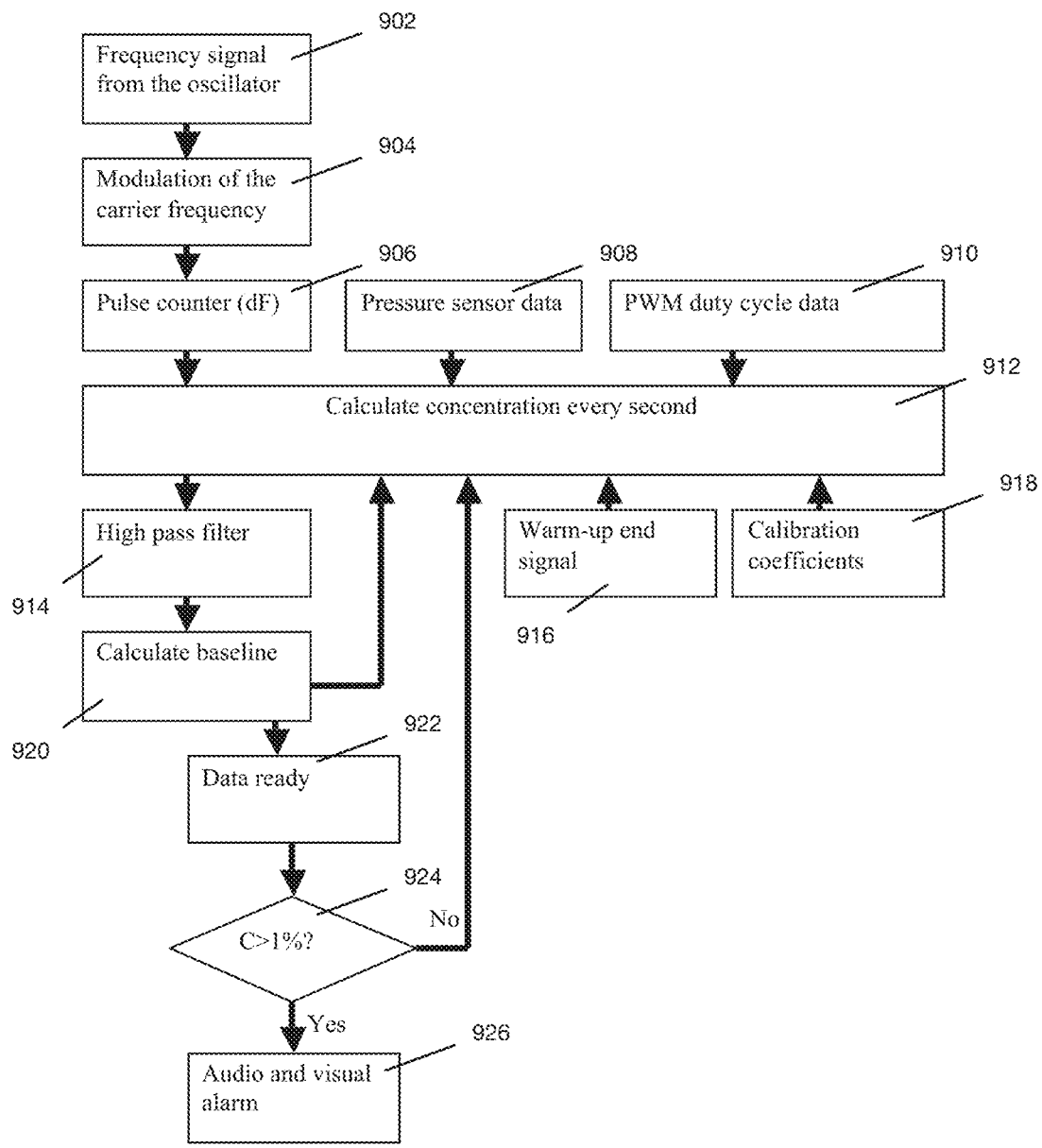
FIG. 9 is a flowchart of the methane concentration calculation algorithm.

FIG. 9 is a flowchart of the methane concentration calculation algorithm. The frequency signal from the oscillator at step 902 is used to modulate the carrier frequency at 904, which is then fed to the pulse counter at 906. That, along with pressure sensor data at 908 and pulse width modulation duty cycle data at 910 are used (along with warm-up end signal 916 and calibration coefficients (918) to calculate the concentration every second at step 912. This is fed to high pass filter at 914, and then the baseline is calculated at 920. When data is ready at 922, it is checked to see if the concentration is greater than 1% at 924. If Yes, then audio and visual alarms are triggered; if No, then the loop feeds back to step 912.

Figure 10:
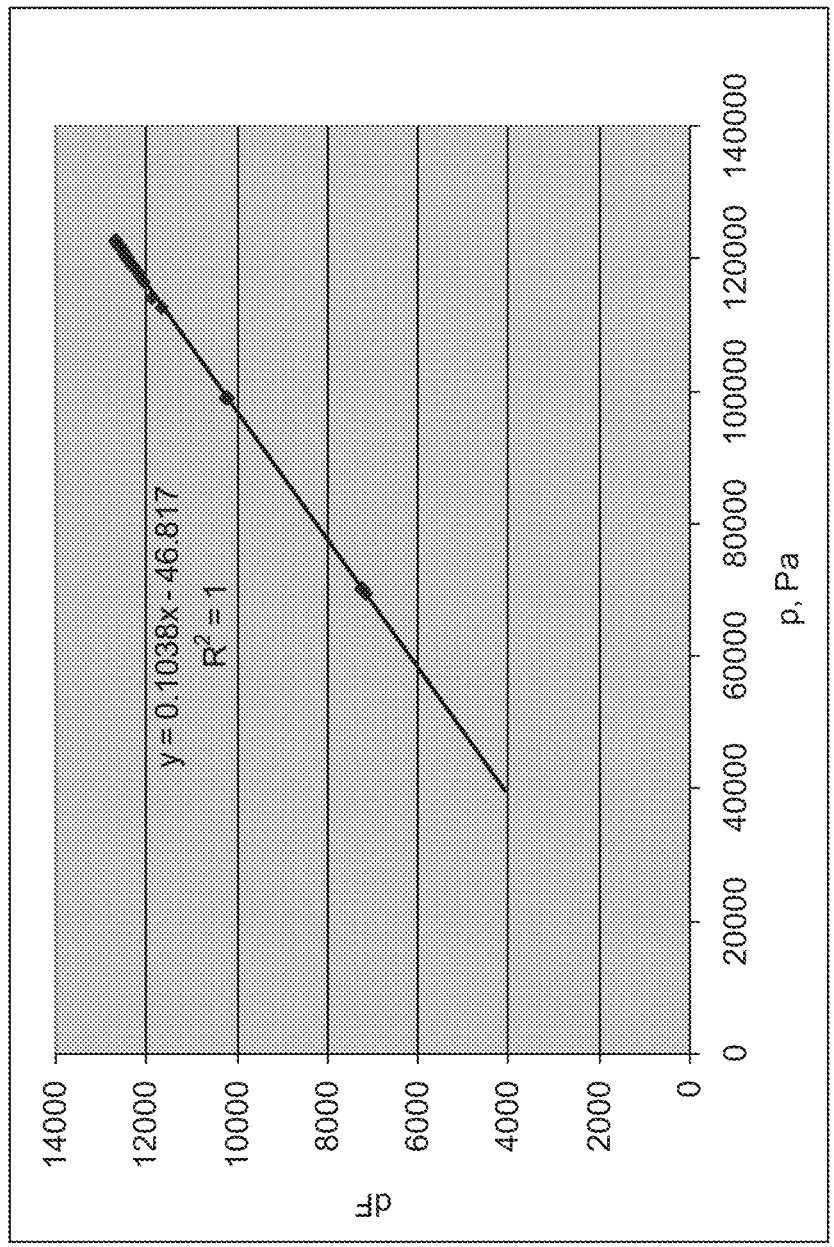
FIG. 10 is a graph of the typical response of the tuning fork oscillator to pressure changes in the preferred embodiment.
Figure 11:
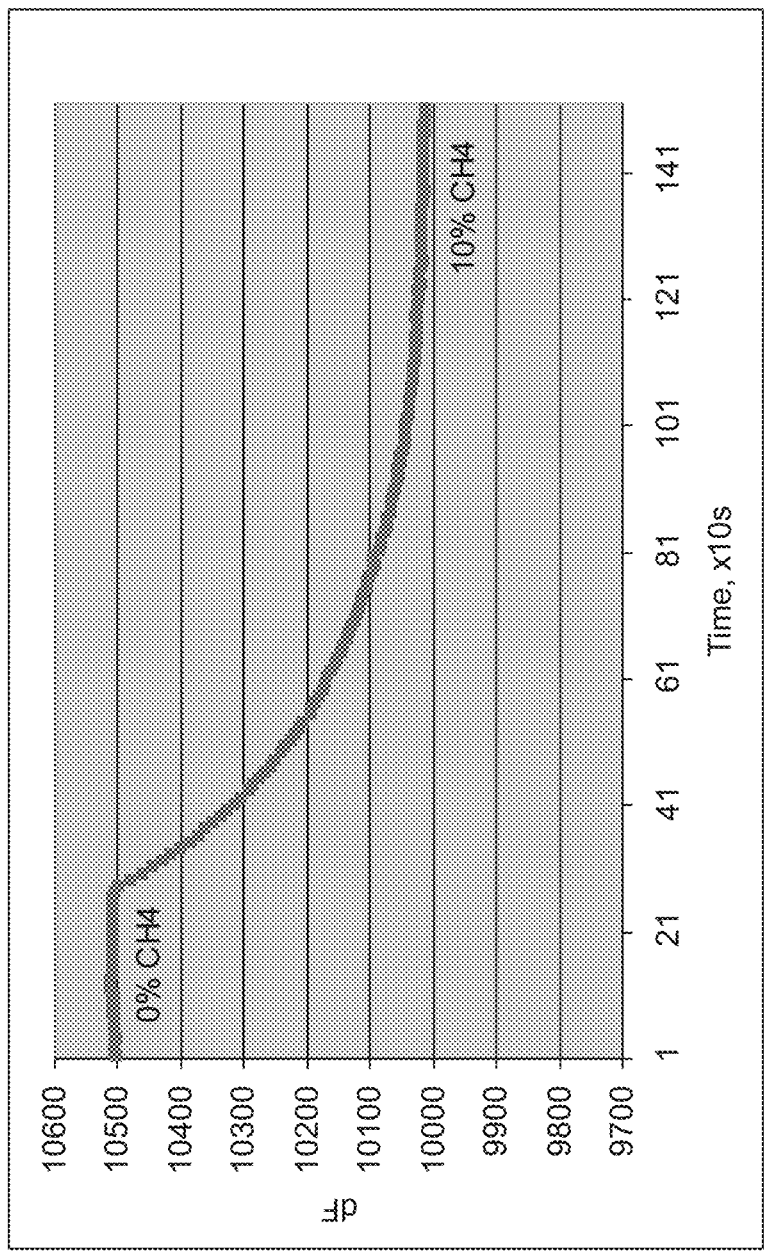
FIG. 11 is a graph of the typical response of the tuning fork oscillator to methane in the preferred embodiment.
Figure 12:
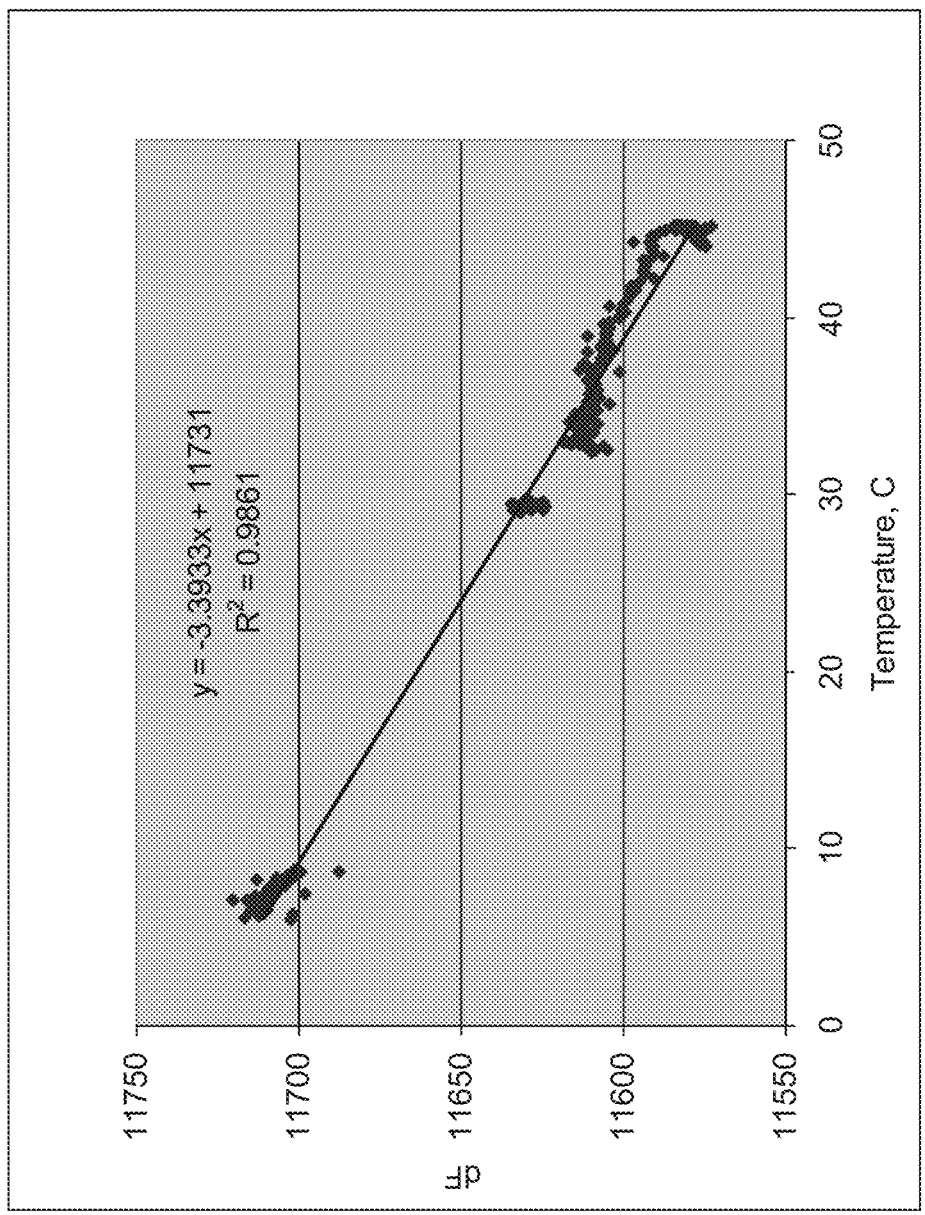
FIG. 12 is a graph of the typical response of the tuning fork oscillator to temperature variations in the preferred embodiment.

For reference purposes, FIG. 10 is a graph of the typical response of the tuning fork oscillator to pressure changes in the preferred embodiment; FIG. 11 is a graph of the typical response of the tuning fork oscillator to methane in the preferred embodiment; and FIG. 12 is a graph of the typical response of the tuning fork oscillator to temperature variations in the preferred embodiment.

The following invention is claimed:

1. An apparatus for detection of methane in an environment, the apparatus comprising
a housing comprising a sensor printed circuit board and a processor printed circuit board interconnected to the sensor printed circuit board,
the sensor printed circuit board comprising
a first tuning fork, and
a second tuning fork, the second tuning fork being exposed to the environment,
wherein the first tuning fork and the second tuning fork are attached to opposite sides of the sensor printed circuit board;
the processor printed circuit board comprising
processing circuitry interconnected to the first tuning fork and the second tuning fork and programmed to
determine a frequency difference between the frequency of vibration of the first tuning fork and the frequency of vibration of the second tuning fork, and
if the frequency difference is greater than a predetermined threshold, then setting an alarm to indicate the presence of methane.

2. The apparatus of claim 1 wherein
the processing circuitry comprises a D flip-flop and a microcontroller, wherein
the vibration frequency signals from the tuning forks are interconnected to the D input and clock input of the D flip-flop for determining the differential frequency,
the trigger output of the D flip-flop is interconnected to the microcontroller that counts pulses within a certain time period by modulating an external high frequency carrier signal;
wherein the number of pulses counted is a nearly linear function of the methane concentration.

3. The apparatus of claim 1 wherein the first tuning fork and the second tuning fork each comprise a quartz oscillator.

4. The apparatus of claim 1 further comprising a casing in which the first tuning fork is located, the casing being vacuum sealed to provide temperature and pressure isolation from the environment.

5. The apparatus of claim 4 further comprising a heating element mounted in proximity to the casing wherein the casing is heated by the heating element.

6. The apparatus of claim 1 further comprising a pressure sensor, a humidity sensor, and a thermistor each mounted within the housing and interconnected with the processing circuitry on the processor printed circuit board.

7. A method for detection of methane in an environment, the method comprising
  providing in a housing
    a sensor printed circuit board, and
    a processor printed circuit board interconnected to the sensor printed circuit board,
  providing on the sensor printed circuit board
    a first tuning fork, and
    a second tuning fork, the second tuning fork being exposed to the environment,
    wherein the first tuning fork and the second tuning fork are attached to opposite sides of the sensor printed circuit board;
  providing on the processor printed circuit board
    processing circuitry interconnected to the first tuning fork and the second tuning fork
    wherein the processing circuitry
      determines a frequency difference between the frequency of vibration of the first tuning fork and the frequency of vibration of the second tuning fork, and
      sets an alarm to indicate the presence of methane if the frequency difference is greater than a predetermined threshold.

8. The method of claim 7 wherein
  the processing circuitry comprises a D flip-flop and a microcontroller,
  the vibration frequency signals from the tuning forks are interconnected to the D input and clock input of the D flip-flop for determining the differential frequency,
  the trigger output of the D flip-flop is interconnected to the microcontroller that counts pulses within a certain time period by modulating an external high frequency carrier signal; and
  the number of pulses counted is a nearly linear function of the methane concentration.

9. The method of claim 7 wherein the first tuning fork and the second tuning fork each comprise a quartz oscillator.

10. The method of claim 7 further comprising providing a casing in which the first tuning fork is located, the casing being vacuum sealed to provide temperature and pressure isolation from the environment.

11. The method of claim 10 further comprising mounting a heating element in proximity to the casing wherein the casing is heated by the heating element.

12. The method of claim 7 further comprising mounting a pressure sensor, a humidity sensor, and a thermistor within the housing and interconnecting them with the processing circuitry on the processor printed circuit board.

* * * * *